US00PP26576P2

(12) United States Plant Patent
Wood

(10) Patent No.: US PP26,576 P2
(45) Date of Patent: Apr. 5, 2016

(54) ***VIBURNUM* PLANT NAMED 'SMVDLS'**

(50) Latin Name: *Viburnum bracteatum*
Varietal Denomination: SMVDLS

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 119 days.

(21) Appl. No.: 13/987,981

(22) Filed: Sep. 20, 2013

(51) Int. Cl.
*A01H 5/02* (2006.01)

(52) U.S. Cl.
USPC ..... Plt./226

(58) Field of Classification Search
USPC ..... Plt./226
See application file for complete search history.

(56) References Cited

PUBLICATIONS

UPOV hit on CA PBR 12-7744, viburnum 'SMVDLS', published Oct. 31, 2012.*

* cited by examiner

*Primary Examiner* — Anne Grunberg
(74) *Attorney, Agent, or Firm* — C. A. Whealy

(57) ABSTRACT

A new and distinct cultivar of *Viburnum* plant named 'SMVDLS', characterized by its compact, upright and somewhat outwardly spreading plant habit; vigorous growth habit; freely branching habit; glossy leaves; large inflorescences with numerous white-colored flowers; dark violet blue-colored fruits; and good container and garden performance.

3 Drawing Sheets

Botanical designation: *Viburnum bracteatum.*
Cultivar denomination: 'SMVDLS'.

BACKGROUND OF THE INVENTION

The present invention relates to a new and distinct cultivar of *Viburnum* plant, botanically known as *Viburnum bracteatum* and hereinafter referred to by the name 'SMVDLS'.

The new *Viburnum* plant is a product of a planned breeding program conducted by the Inventor in Grand Haven, Mich. The objective of the breeding program is to develop new compact *Viburnum* plants with good container performance and unique leaf types.

The new *Viburnum* plant originated from an open-pollination during the summer of 2007 of *Viburnum bracteatum* 'Emerald Lustre', not patented, as the female, or seed, parent with an unknown selection of *Viburnum bracteatum* as the male, or pollen, parent. The new *Viburnum* plant was discovered and selected by the Inventor in 2009 as a single flowering plant from within the progeny of the stated open-pollination in a controlled environment in Grand Haven, Mich.

Asexual reproduction of the new *Viburnum* plant by softwood cuttings in a controlled environment in Grand Haven, Mich. since June, 2009 has shown that the unique features of this new *Viburnum* plant are stable and reproduced true to type in successive generations of asexual reproduction.

SUMMARY OF THE INVENTION

Plants of the new *Viburnum* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'SMVDLS'.

These characteristics in combination distinguish 'SMVDLS' as a new and distinct *Viburnum* plant:

1. Compact, upright and somewhat outwardly spreading plant habit.
2. Vigorous growth habit.
3. Freely branching habit.
4. Glossy leaves.
5. Large inflorescences with numerous white-colored flowers.
6. Dark violet blue-colored fruits.
7. Good container and garden performance.

Plants of the new *Viburnum* can be compared to plants of the female parent, 'Emerald Lustre'. Plants of the new *Viburnum* differ from plants of 'Emerald Lustre' in the following characteristics:

1. Plants of the new *Viburnum* are more compact than plants of 'Emerald Lustre'.
2. Leaves of the new *Viburnum* are glossier than leaves of plants of 'Emerald Lustre'.
3. Inflorescences of plants of the new *Viburnum* are more compressed than inflorescences of 'Emerald Lustre'.

Plants of the new *Viburnum* can be compared to plants of the *Viburnum bracteatum* 'SMVDBL', disclosed in U.S. Plant patent application Ser. No. 13/987,980. Plants of the new *Viburnum* differ from plants of 'SMVDBL' in the following characteristics:

1. Plants of the new *Viburnum* are not as freely branching as plants of 'SMVDBL'.
2. Plants of the new *Viburnum* have larger inflorescences with more flowers per inflorescence than plants of 'SMVDBL'.

BRIEF DESCRIPTION OF THE PHOTOGRAPHS

The accompanying colored photographs illustrate the overall appearance of the new *Viburnum* plant showing the colors as true as it is reasonably possible to obtain in colored reproductions of this type. Colors in the photographs may differ slightly from the color values cited in the detailed botanical description which accurately describe the colors of the new *Viburnum* plant.

The photograph on the first sheet is a side perspective view of a typical plant of 'SMVDLS' grown in a container.

The photograph on the second sheet is a close-up view of a typical flowering plant of 'SMVDLS'.

The photograph on the third sheet is a close-up view of a typical plant with berries of 'SMVDLS'.

DETAILED BOTANICAL DESCRIPTION

The aforementioned photographs and following observations, measurements and values describe plants of the new *Viburnum* grown in three-gallon containers during the summer in an outdoor nursery in Grand Haven, Mich. and under cultural practices typical of commercial *Viburnum* production. Plants were four years old when the photographs and the description were taken. In the description, color references are made to The Royal Horticultural Society Colour Chart, 1995 Edition, except where general terms of ordinary dictionary significance are used.

Botanical classification: *Viburnum bracteatum* 'SMVDLS'.

Parentage:

*Female, or seed, parent.*—*Viburnum bracteatum* 'Emerald Lustre', not patented.

*Male, or pollen, parent.*—Unknown selection of *Viburnum bracteatum*, not patented.

Propagation:

*Type.*—By softwood cuttings.

*Time to initiate roots, summer.*—About 30 days at 24° C.

*Time to produce a rooted young plant, summer.*—About four months at 24° C.

*Root description.*—Fine to thick; white and brown in color.

*Rooting habit.*—Freely branching; dense.

Plant description:

*Plant and growth habit.*—Deciduous perennial shrub; compact, upright and somewhat outwardly spreading plant habit; vigorous growth habit.

*Branching habit.*—Freely branching habit with about 20 lateral branches developing per plant; pinching (removal of terminal apices) will enhance lateral branch development.

*Plant height.*—About 60 cm.

*Plant diameter* (*area of spread*).—About 60 cm.

Lateral branch description:

*Length.*—About 40 cm.

*Diameter.*—About 3 mm.

*Internode length.*—About 7.5 cm.

*Texture.*—Pubescent.

*Strength.*—Strong.

*Aspect.*—Erect to about 20° from vertical.

*Color.*—Close to 199B.

Leaf description:

*Arrangement.*—Opposite, simple.

*Length.*—About 7.5 cm.

*Width.*—About 6 cm.

*Shape.*—Ovate.

*Apex.*—Acute.

*Base.*—Cordate.

*Margin.*—Crenate; ruffled.

*Texture, upper surface.*—Rugose, glabrous.

*Texture, lower surface.*—Pubescent; coarse.

*Venation pattern.*—Pinnate.

*Color.*—Developing leaves, upper and lower surfaces: Close to 146A. Fully expanded leaves, upper surface: Close to 137A; venation, close to 145A; glossy. Fully expanded leaves, lower surface: Close to 137B; venation, close to 145C.

*Petiole.*—Length: About 1 cm. Diameter: About 2 mm. Texture, upper and lower surfaces: Pubescent. Color, upper and lower surfaces: Close to 145A.

Flower description:

*Flower appearance and arrangement.*—Single rotate flowers arranged in terminal cymes; freely flowering habit with usually about 283 flowers per inflorescence; flowers face upright to outwardly.

*Natural flowering season.*—Flowering commences in June in Michigan; flowers last about two to four weeks on the plant; flowers not persistent.

*Fragrance.*—Slightly fragrant; sweet, pleasant.

*Inflorescence height.*—About 4.5 cm.

*Inflorescence diameter.*—About 5.5 cm.

*Flower diameter.*—About 3.5 mm.

*Flower length* (*height*).—About 2 mm.

*Flower buds.*—Length: About 1 mm. Diameter: About 1 mm. Shape: Globose. Color: Close to 142B to 142C.

*Petals.*—Quantity per flower: Five petals in a single whorl. Length: About 1.8 mm. Width: About 1.5 mm. Shape: Obovate. Apex: Obtuse. Margin: Entire. Texture, upper and lower surfaces: Smooth, glabrous. Color: When opening, upper and lower surfaces: Close to 155D. Fully opened, upper and lower surfaces: Close to 155D.

*Sepals.*—Sepal development has not been observed on plants of the new *Viburnum*.

*Peduncles.*—Length: About 2 cm. Diameter: About 4 mm. Strength: Strong. Aspect: Mostly erect. Texture: Smooth. Color: Close to 141C.

*Pedicels.*—Length: About 7.5 mm. Diameter: About 3 mm. Strength: Strong. Aspect: Erect to about 80° from peduncle axis. Texture: Smooth. Color: Close to 141C.

*Reproductive organs.*—Androecium: Quantity per flower: About five. Anther shape: Irregularly globular. Anther length: About 1 mm. Anther color: Close to 155A. Amount of pollen: Slight. Pollen color: Close to 155D. Gynoecium: Quantity per flower: One. Pistil length: About 2 mm. Style length: About 1.8 mm. Style color: Close to 143D. Stigma shape: Rounded. Stigma color: Close to 143D. Ovary color: Close to 143D. Fruits: Length: About 5 mm. Diameter: About 5 mm. Shape: Spherical. Texture: Smooth, glossy luster. Color, immature: Close to 143C. Color, mature: Close to 103B to 103C. Seeds: Length: About 4.8 mm. Diameter: About 3 mm. Texture: Smooth. Color: Close to 177C.

Garden performance: Plants of the new *Viburnum* have been observed to have good garden and container performance and to tolerate rain, wind and temperatures ranging from about −27° C. to about 40° C.

Pathogen & pest resistance: Plants of the new *Viburnum* have not been observed to be resistant to pathogens and pests common to *Viburnum* plants.

It is claimed:

1. A new and distinct *Viburnum* plant named 'SMVDLS' as illustrated and described.

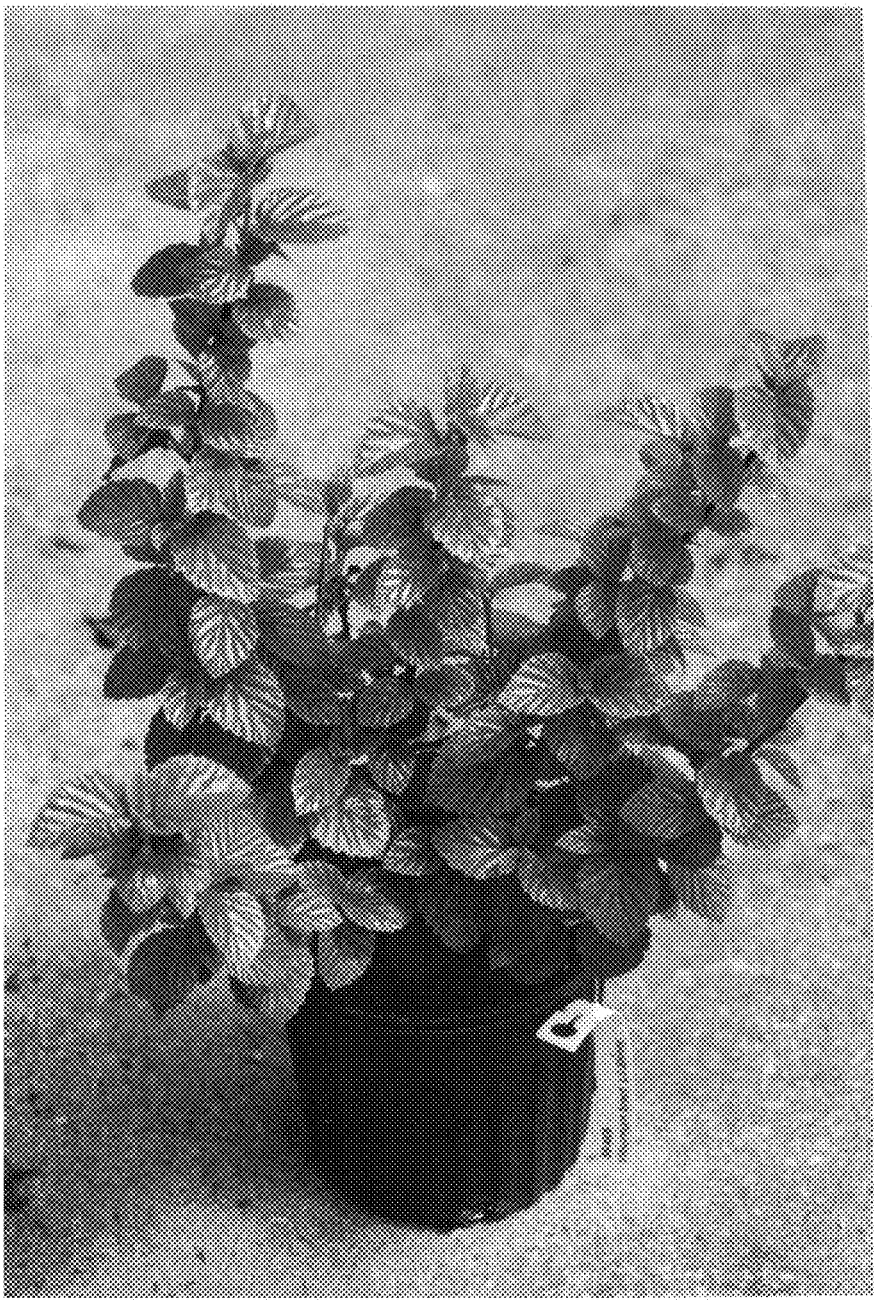

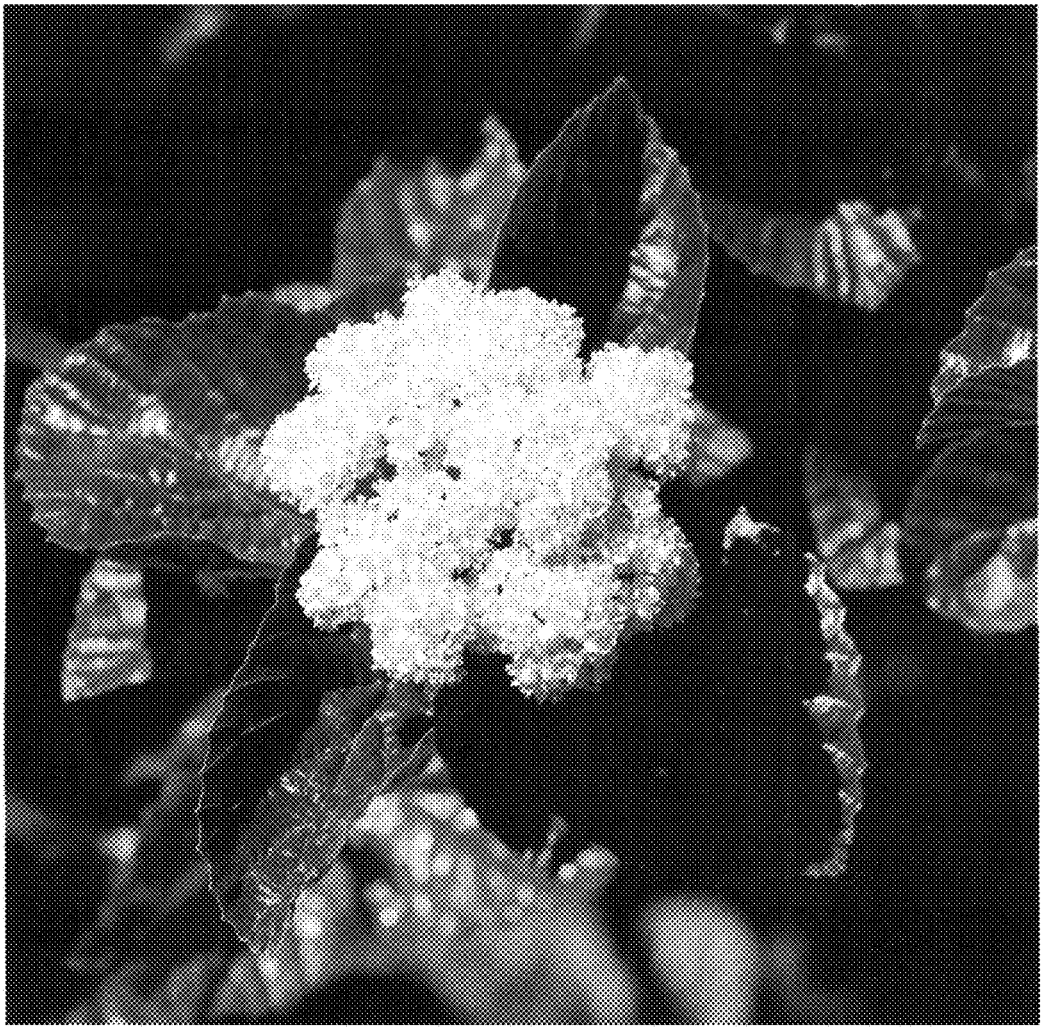

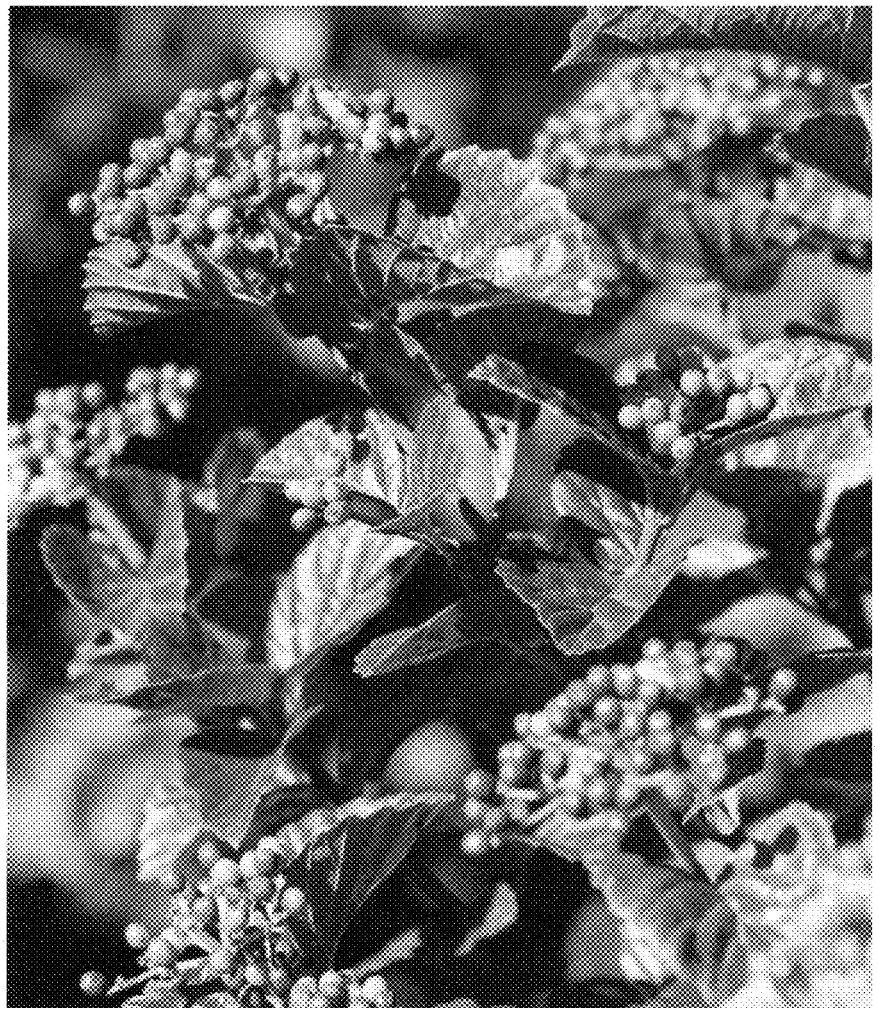

* * * * *